United States Patent [19]

Dingwall et al.

[11] Patent Number: 4,908,465

[45] Date of Patent: * Mar. 13, 1990

[54] SUBSTITUTED PROPANE-PHOSPHONOUS ACID COMPOUNDS

[75] Inventors: John G. Dingwall, Pantaleon; Josef Ehrenfreund, Allschwil, both of Switzerland; Roger G. Hall, Chorlton-cum Hardy; James Jack, Stockport, both of England

[73] Assignee: Ciba-Geigy Corporation, Ardsley, N.Y.

[ * ] Notice: The portion of the term of this patent subsequent to Sep. 20, 2005 has been disclaimed.

[21] Appl. No.: 203,851

[22] Filed: Jun. 7, 1988

Related U.S. Application Data

[62] Division of Ser. No. 940,836, Dec. 12, 1986, Pat. No. 4,772,738, which is a division of Ser. No. 787,300, Oct. 15, 1985, Pat. No. 4,656,298.

[30] Foreign Application Priority Data

Dec. 10, 1984 [GB] United Kingdom ................. 8425872

[51] Int. Cl.$^4$ .............................................. C07F 9/48
[52] U.S. Cl. .................................................. 558/175
[58] Field of Search .......................................... 558/175

[56] References Cited

U.S. PATENT DOCUMENTS

| | | | |
|---|---|---|---|
| 2,535,175 | 12/1950 | Tawney .............................. | 558/175 |
| 3,374,288 | 3/1968 | Lange ................................. | 260/857 |
| 3,637,763 | 1/1972 | Firestone ........................... | 558/175 |
| 3,784,590 | 1/1974 | Firestone ........................... | 558/175 |
| 3,970,586 | 7/1976 | Schliebr et al. .................... | 558/175 |
| 4,399,287 | 8/1983 | Baillie et al. ...................... | 558/175 |

FOREIGN PATENT DOCUMENTS

| | | |
|---|---|---|
| 9348 | 4/1980 | European Pat. Off. . |
| 68497 | 1/1983 | European Pat. Off. . |
| 93081 | 11/1983 | European Pat. Off. . |
| 166693 | 12/1964 | U.S.S.R. .............................. 558/175 |
| 463675 | 10/1975 | U.S.S.R. .............................. 558/175 |
| 1174439 | 8/1985 | U.S.S.R. . |

OTHER PUBLICATIONS

Kreutzkamp et al., "Chem. Abstracts," vol. 57 (1962), cols. 5946 and 5947.
J. Med. Chem., vol. 27, pp. 654–659 (1984).
Aust. J. Chem., vol. 33, pp. 287–294 (1980).

*Primary Examiner*—J. E. Evans
*Attorney, Agent, or Firm*—Irving M. Fishman; JoAnn Villamizar

[57] ABSTRACT

The compounds of the formula

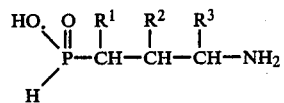

in which one of the groups $R^1$, $R^2$ and $R^3$ represents hydrogen, $C_{1-8}$-alkyl, $C_{3-6}$-cycloalkyl, phenyl optionally substituted by halogeno, $C_{1-4}$-alkyl, $C_{1-4}$-alkoxy and/or trifluoromethyl, or $C_{7-10}$-phenylalkyl optionally substituted in the phenyl moiety by halogeno, $C_{1-4}$-alkyl, $C_{1-4}$-alkoxy and/or trifluoromethyl, and the other two are hydrogen, or salts thereof.

These compounds have valuable pharmaceutical properties.

5 Claims, No Drawings

SUBSTITUTED PROPANE-PHOSPHONOUS ACID COMPOUNDS

This is a Divisional of application Ser. No. 940,836 filed on Dec. 12, 1986, now U.S. Pat. No. 4,772,738, which is a Divisional of Ser. No. 787,300 filed Oct. 15, 1985 now U.S. Pat. No. 4,656,298.

The present invention relates to new 3-aminopropanephosphonous acids, processes for their production and their use as pharmaceuticals.

The present invention provides compounds of the formula I,

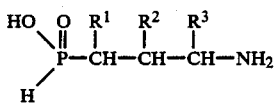

in which one of the groups $R^1$, $R^2$ and $R^3$ represents hydrogen, $C_{1-8}$-alkyl, $C_{3-6}$-cycloalkyl, phenyl optionally substituted by halogen, $C_{1-4}$-alkyl, $C_{1-4}$-alkoxy and/or trifluoromethyl, or $C_{7-10}$-phenylalkyl optionally substituted in the phenyl moiety by halogeno, $C_{1-4}$-alkyl, $C_{1-4}$-alkoxy and/or trifluoromethyl, and the other two are hydrogen; as well as salts thereof.

A phenyl group may have one or more than one, preferably at most two of the same or different substituents.

Alkyl may be e.g. methyl, ethyl, n-propyl, isopropyl, n-butyl, sec-butyl (2-methylpropyl) or t-butyl, as well as n-pentyl, n-hexyl, n-heptyl or n-octyl.

Cycloalkyl may be e.g. cyclopropyl, cyclobutyl or cyclopentyl but is preferably cyclohexyl.

Alkoxy may be e.g. methoxy, ethoxy, n-propoxy, isopropoxy, n-butoxy, sec-butoxy or t-butoxy.

Halogeno is preferably fluoro or chloro, as well as bromo.

Phenylalkyl groups are e.g. benzyl, 1- or 2-phenylethyl, 2- or 3-phenylpropyl or 4-phenylbutyl groups, each optionally substituted in the phenyl portion as described hereinbefore.

Salts of the compounds of the formula I are particularly pharmaceutically acceptable salts thereof, such as the corresponding addition salts with acids, as well as the salts with bases. Suitable acids for the formation of acid addition salts are, for example, mineral acids, such as hydrochloric, hydrobromic, sulphuric or phosphoric acid, or organic acids, such as organic sulphonic acids, for example, benzenesulphonic, 4-toluenesulphonic or methanesulphonic acid, and organic carboxylic acids, such as acetic, lactic, palmitic, stearic, malic, maleic, fumaric, tartaric, ascorbic or citric acid. Salts with bases are, for example, alkali metal or alkaline earth metal salts, such as sodium, potassium, calcium or magnesium salts, or ammonium salts, such as those with ammonia or suitable organic amines, e.g. diethylamine, di-(2-hydroxyethyl)-amine or tri-(2-hydroxyethyl)-amine. The compounds of the formula I may also form inner salts.

Depending on the presence of asymmetric carbon atoms, the compounds of this invention may be in the form of mixtures of isomers, particularly racemates, or in the form of pure isomers, particularly optical antipodes.

Preferred are compounds of formula I, wherein $R^1$ and $R^3$ are each hydrogen and $R^2$ is hydrogen, phenyl optionally substituted as hereinbefore defined, especially hydrogen, or halogeno-phenyl, and most especially hydrogen or primarily 4-chlorophenyl or 4-fluorophenyl; or salts, such as pharmaceutically acceptable salts thereof.

The present invention also provides a first process for the production of compounds of formula I comprising, in a precursor compound of formula II

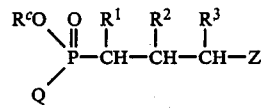

in which $R^1$, $R^2$ and $R^3$ have their previous significance, Z is $-NH_2$ or a protected amino group $Z^o$, Q is hydrogen or a protecting group $Q^o$, and $R^c$ is hydrogen, $C_{1-4}$-alkyl, or an alkali metal or ammonium cation, replacing the group $R^c$, when it is alkyl, by hydrogen or by an alkali metal or ammonium cation, and replacing the group Q, when it is a protecting group $Q^o$, by hydrogen, and converting the group Z, when it is a protected amino group $Z^o$, into $-NH_2$, to produce a compound of formula I.

Depending on the groups involved, the replacement and conversion operations may be carried out in any sequence or simultaneously by methods which are well-known per se.

If desired, a resulting salt may be converted into the free compound or into another salt and/or, if desired, a resulting free compound may be converted into a salt and/or, if desired, a resulting mixture of isomers may be separated into the single isomers.

Typical protected amino groups $Z^o$ are acylamino groups such as acetylamino, phthalimido, benzyloxycarbonylamino or tert-butoxy-carbonylamino groups or 1-aryl-$C_{1-4}$-alkylamino groups e.g. benzylamino.

Optional protecting groups $Q^o$ are those known in the art and described in EP 0,009,348 and Aust. J. Chem. 33, 292 (1980), e.g. groups having the formula $-C(C_{1-4}\text{-alkyl})(OR^a)OR^b$, in particular groups having the formula $-CH(OR^a)OR^b$ in which $R^a$ and $R^b$ are each $C_{1-4}$-alkyl and especially a group having the formula $-CH(OC_2H_5)_2$.

The replacement of an alkyl group $R^c$ in compounds of formula II by hydrogen may be effected by treatment with a suitable nucleophilic reagent such as an alkali metal hydroxide, e.g. sodium hydroxide, an alkali metal halide, particularly bromide or iodide such as lithium bromide or sodium iodide, thiourea, an alkali metal thiophenolate such as sodium thiophenolate. The replacement reaction may be carried out in the absence or presence of a solvent and, if necessary, while cooling or heating, in a closed vessel and/or under an atmosphere of an inert gas.

The replacement of the group $Q^o$ and/or the group $R^c$ in which $R^c$ is $C_{1-4}$-alkyl in compounds of formula II by hydrogen may be effected by treatment with an acid under hydrolytic conditions, especially with a mineral acid such as a hydrohalic acid e.g. hydrochloric acid which is used in dilute or concentrated aqueous form, or by treatment with an organic silyl halide such as trimethyl-silyl iodide or bromide, followed by hydrolysis. The reaction is preferably conducted at elevated temperature e.g. while refluxing the reaction mixture and, if necessary using an organic diluent, in a closed vessel and/or under an atmosphere of an inert gas.

Protected amino group $Z^o$ may be converted into free amino according to known methods, which are selected according to the characteristics of the protected amino group to be converted into amino, such as solvolytic or hydrogenolytic procedures, for example, hydrolysis in the presence of an acid or a base, acidolysis, e.g. treatment with trifluoroacetic acid, treatment with hydrazine, or hydrogenolysis in the presence of a metallic hydrogenation catalyst, or any other suitable procedure, provided that the hydrogenation/catalyst method cannot be employed for compounds of formula II wherein Q is hydrogen.

It is preferred that all protecting groups are converted, $R^c$ and $Q^o$ each being converted to H and $Z^o$ being converted to $NH_2$, in a single step, by treatment with an acid, preferably a hydrohalic acid, especially hydrochloric acid, under hydrolytic conditions.

The starting materials of formula II are new compounds, and form part of the present invention. Thus starting materials of formula II wherein $R^1$, $R^2$, $R^3$, $R^c$, Q and Z have their previous significance, provided that, when $R^2$ and Q are each hydrogen $R^c$ may not be alkyl, are new compounds and form part of this invention. The new compounds of formula II may be prepared, for example, by various methods according to the nature of the group X in the formula IV defined hereinafter, by reacting, in the presence of a basic catalyst or in the presence of agents forming free radicals, a compound of the formula III,

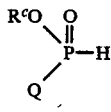
III in which $R^c$ and Q have their previous significance, with a compound of formula IV,

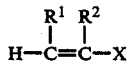
IV in which $R^1$ and $R^2$ have their previous significance and X is a group capable of being converted into a group of formula Ia,

Ia wherein $R^3$ and Z have their previous significance, in order to produce a compound of formula V,

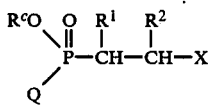
V wherein $R^1$, $R^2$, $R^c$, Q and X have their previous significance, and then converting the group X into a group of formula Ia, to produce a compound of formula II.

A group X is primarily cyano but may also represent carbamoyl, a group of formula Ib,

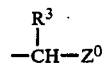
Ib in which $R^3$ and $Z^o$ have their previous significance; or X is a group of formula Ic,

Ic in which $R^3$ has its previous significance and

is an optionally functionally modified carbonyl group such as a corresponding ketal or thioketal group, including a corresponding cyclic group.

When, in a compound of formula III, Q is a protecting group $Q^o$ and $R^c$ is $C_{1-4}$-alkyl and, in the compound of formula IV, X is an activating group Xa such as cyano or

then either a basic catalyst or a free radical catalyst may be employed. When, however, the same compounds of formula III are reacted with compounds of formula IV in which X is e.g. a residue of formula Ib, then free radical catalysts are required.

A basic catalyst used in the first step may be e.g. an alkali metal $C_{1-4}$-alkoxide, for example, a sodium or potassium $C_{1-4}$-alkoxide, in particular sodium methoxide, sodium ethoxide or potassium tert-butoxide, an alkaline or alkaline earth metal fluoride, such as potassium fluoride or caesium fluoride, or an alkali metal hydride, such as sodium hydride. The reaction may be effected with or without the use of an added solvent. If a solvent is added, this is preferably ably an alcohol, in particular a $C_{1-4}$-alkanol corresponding to the alkoxide used as basic catalyst. The reaction temperature may vary from 0° C. to the boiling point of any added solvent.

Agents forming free radicals are, for example, ionizing and ultra-violet radiation, peroxy compounds, such as inorganic peroxy compounds, e.g. hydrogen peroxide or ammonium persulfate, or organic peroxides, e.g. benzoyl peroxide or tert-butyl peroxide, or organic azo compounds, e.g. azo-bis-isobutyronitrile. Reactions involving free radical-forming agents may be conducted in the optional presence of a solvent and, if necessary, while cooling or heating, in a closed vessel and/or in an atmosphere of an inert gas.

The conversion of a group X into the group Ia is carried out according to known methods. Cyano and carbamoyl are converted into aminomethyl by reduction, cyano, for example, by hydrogenation in the presence of a suitable catalyst, e.g. Raney nickel and of a solvent, such as ethanol, which may preferably contain ammonia, and carbamoyl, for example, by treatment with a suitable hydride reducing agent, such as borane in tetrahydrofuran, provided that the hydrogenation/- catalyst method cannot be employed for compounds of formula V in which Q is hydrogen.

Protected amino group $Z^o$ may be converted into $-NH_2$ as described hereinbefore.

The conversion of a group X in the compounds of formula V, in which X is a group Ic, in which Y is oxygen, into the group of the formula Ia is carried out by known reductive amination procedures, e.g. treatment with sodium cyanoborohydride in the presence of ammonium acetate in a suitable solvent, such as dioxane, and while cooling, e.g. at about 0° C.

Compounds of formula III are either known or can be prepared by known methods viz. those described in Aust. J. Chem. 33, 292 (1980) or EP 0,009,348.

Compounds of formula IV are either known or can be prepared by known methods.

Specific examples of compounds of formula III include:
methyl (dimethoxymethyl)phosphonite,
ethyl (dimethoxymethyl)phosphonite,
n-propyl (dimethoxymethyl)phosphonite,
i-propyl (dimethoxymethyl)phosphonite,
n-butyl (dimethoxymethyl)phosphonite
methyl (diethoxymethyl)phosphonite
n-propyl (diethoxymethyl)phosphonite,
n-butyl (diethoxymethyl)phosphonite
methyl (1,1-dimethoxyethyl)phosphonite
ethyl (1,1-dimethoxyethyl)phosphonite
ethyl (1,1-diethoxyethyl)phosphonite
methyl (1,1-dimethoxybutyl)phosphonite
preferred are methyl (dimethoxymethyl)phosphonite,
ethyl (diethoxymethyl)phosphonite,
methyl (1,1-dimethoxyethyl)phosphonite,
ethyl (1,1-diethoxyethyl)phosphonite
especially preferred is ethyl (diethoxymethyl)phosphonite.

The compounds of the formula V in which Q is $Q^o$ particularly those, in which X is a cyano group or represents a group of the formula Ic, may also be prepared by reacting a compound of the formula VI,

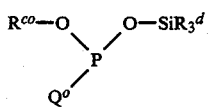   VI in which $Q^o$ has its previous significance, $R^{co}$ is $C_{1-4}$-alkyl and each $R^d$ independently is $C_{1-6}$-alkyl, preferably $C_{1-2}$-alkyl particularly methyl, the groups $R^{co}$ and $R^d$ being the same or different, with a compound of the formula VII,

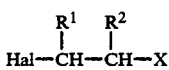   VII in which $R^1$ and $R^2$ have their previous significance and X has the previously given meaning, but is primarily cyano or a group of the formula Ic, and Hal stands for halogeno, such as iodo, bromo or chloro. The reaction is preferably carried out under the conditions of the Arbusov method, e.g. at a reaction temperature ranging from room temperature to an elevated temperature, e.g. 160° C., while removing the trialkyl silyl halide formed in the reaction.

Furthermore the compounds of formula V in which Q is $Q^o$ and X is an activating group Xa such as cyano or

may be prepared by reacting a compound of formula VI, as defined above, with a compound of formula IV wherein $R^1$, $R^2$ and X have their previous significance. The reaction is preferably conducted under the general conditions of the Michael addition reaction, e.g. at a temperature range between room temperature and 80° C., in the presence or, more likely, in the absence of an inert solvent.

The silyl reagents of the formula VI are new and form part of this invention. Preferred compounds of formula VI are those having the formula VIA,

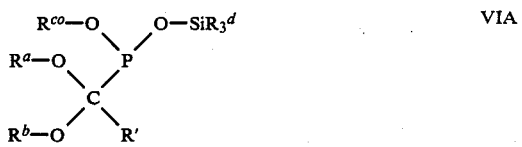   VIA wherein $R^a$, $R^b$, $R^{co}$ and $R^d$ have their previous significance and $R^4$ is hydrogen or $C_{1-4}$-alkyl, such as ethyl trimethylsilyl (diethoxymethyl)phosphonite, methyl trimethylsilyl (dimethoxymethyl)phosphonite, or ethyl trimethylsilyl (1,1-diethoxyethyl)phosphonite.

The compounds of formula VI may be prepared by reaction, optionally in the presence of basic catalyst, of a compound having the formula III in which Q is $Q^o$ and $R^c$ is alkyl, viz. a compound having the formula IIIA

   IIIA in which $Q^o$ and $R^{co}$ have their previous significance; preferably a compound having the formula IIIB

   IIIB in which $R^{co}$, $R^a$ and $R^b$ have their previous significance and $R^4$ is hydrogen or $C_{1-4}$-alkyl, with an appropriate silylating agent, e.g. trimethylsilyl chloride, dimethyl-tert-butyl-silyl chloride or dimethyl(2,3-dimethyl-2-butyl)silylchloride in the presence of a tertiary base, e.g. pyridine or triethyl-amine, hexamethyl disilazane, 1-trimethylsilyl-imidazole, or 1-(dimethyl-tert-butyl-silyl)-imidazole, or any other suitable silylating agent.

The process conditions employed vary depending on the particular silylating agent used. The reaction temperature ranges from about −20° C. to about 150° C., and the reaction may be conducted with or without the use of an inert solvent, such as e.g. diethyl ether, toluene, tetrahydrofuran or dioxan. Alternatively, an excess of the silylating agent may be used as diluent. While the molar ratio of the silylating agent to the compound of the formula IIIA or IIIB is conveniently 1:1, molar excess amounts of the silylating agent may be used to advantage in certain cases.

Compounds of formula VII are either known or may be prepared by known methods.

The compounds of formula I may also be prepared by, in a compound having the formula VIII,

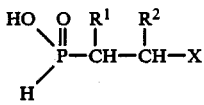 VIII in which $R^1$, $R^2$ and X have their previous significance, converting the group X into a group of formula Id,

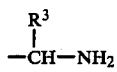 Id wherein $R^3$ has its previous significance, to produce a compound of formula I.

The conversion of the group X into a group of formula Id may be effected by any of the methods described hereinbefore in relation to the production of starting materials of formula II.

The above reaction is carried out according to known methods, in the absence or presence of a solvent, which may also serve as a reagent, if necessary, while cooling or heating, in a closed vessel and/or in the atmosphere of an inert gas.

The starting materials of the formula VIII may be prepared, for example, from compounds of the formula V by converting the group $R^c$—O— into hydroxy, the reaction being carried out according to the previously described procedure, e.g. by acidic hydrolysis, such as by treatment with an aqueous mineral acid, e.g. hydrochloric acid, or by treatment with a nucleophilic reagent and simultaneously or subsequently converting any group Q which is $Q^o$ into hydrogen.

Compounds of formula II in which $R^1$, $R^2$, $R^3$ have their previous significance, $R^c$ is $R^{co}$ and Q is $Q^o$ which has its previous significance may also be prepared by reducing a compound of formula IX

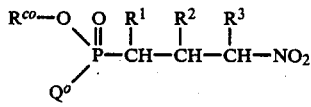 IX by known methods e.g. by catalytic hydrogenation.

Compounds of formula IX may be prepared by reacting a compound of formula X

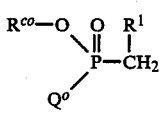 X in the form of the anion XI,

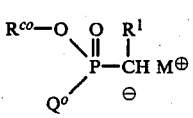 XI in which $R^1$, $Q^o$ and $R^{co}$ have their previous significance and M is an alkali or transition metal atom, preferably lithium with a compound of formula XII,

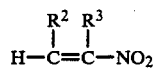 XII in which $R^2$ and $R^3$ have their previous significance. Compounds of formula XI may be prepared by reacting a compound of formula X with a base containing a metal atom M wherein M has its previous significance.

Compounds of formula IX and the process for their preparation are new and form part of this invention.

The base used in the first step may be e.g. a $C_{1-4}$-alkyl lithium, a $C_{2-4}$-alkyl lithium amide or a metal amide, preferably lithium diisopropylamide. The reaction may be effected with the use of an aprotic solvent, preferably an ether, in particular tetrahydrofuran. The reaction temperature may vary from $-78°$ C. to room temperature, under an atmosphere of inert gas.

The compounds of formula X are known (EP 0,009,348) or may be prepared by known methods.

Compounds of formula XII are known and may be prepared by known procedures.

Compounds of formula V,

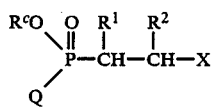 V wherein $R^c$ and $R^2$ have their previous significance, Q is a protecting group $Q^o$ wherein $Q^o$ has its previous significance, $R^1$ is hydrogen and X is an activating group Xa selected from groups X as hereinbefore defined and being a group capable of being converted into a group of formula Ia, —CH($R^3$)—Z, wherein $R^3$ is H and Z has its previous significance, may also be prepared by reacting a compound of formula VA

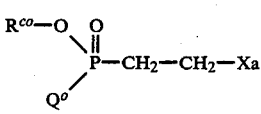 VA in the form of the anion VB

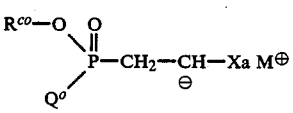 VB wherein $Q^o$, $R^{co}$ and M, Xa have their previous significance with a compound of formula XIII $$LR^2 \qquad \text{XIII}$$

in which $R^2$ has its previous significance and L is a leaving group e.g. halogeno or tosyl. Said process as a means of introducing the group $R^2$ is of value merely if $R^2$ is different from hydrogen.

The starting materials of formula VA are known or may be prepared according to methods described for known compounds of formula Va for example the methods described in European Patent Application EP 0,009,348.

Depending on the process conditions used, the compounds of the formula I are obtained in free form (Zwitterion) or in the form of their salts. The free compounds can be obtained from the salts in a manner known per se, the acid addition salts by treatment with suitable basic reagents, and the salts with bases by treatment with suitable acidic reagents. Acid addition salts can be obtained from the free compounds by reaction with acids or anion exchange preparations, salts with bases by treatment of the free compounds with bases or suitable cation exchange techniques.

The compounds, including their salts, can also be obtained in the form of their hydrates, or include other solvents used for the crystallization.

Due to the close relationship between the new compounds in free form and in the form of their salts, hereinbefore and hereinafter the term "free compounds" shall, if desired, also include the salts thereof, and the term "salts" shall, if desired also include the free compounds, where appropriate according to meaning and purpose.

Mixtures of isomers of compounds of the formula I may be separated into the single isomers according to known methods. Racemates may be resolved, using known classical techniques, into individual optical antipodes, forming diastereomeric salts, using e.g. optically active salt-forming acids, such as (+)- or (−)-tartaric acid or D-(+)-camphor sulfonic acid, or optically active salt-forming bases, e.g. (+)- or (−)-α-methylbenzylamine, separating the diastereomeric salts and liberating the desired free optical antipodes from the separated salts.

The invention relates also to those embodiments of the process, in which a compound obtained as an intermediate at any stage of the process is used as starting material and the remaining process steps are carried out, or in which a starting material is formed under the reaction conditions or is used in the form of a derivative, for example, a salt.

In the process of the present invention, the starting materials used are preferably those that result in the compounds described at the beginning as especially valuable.

The compounds of this invention have been found to have very strong affinities towards $GABA_B$ receptor sites with inhibitory concentrations of 1 to 100 nmol/l. Activity of at least 20 times more pronounced than that of baclofen is observed with the compound of example 1. Agonists at the $GABA_B$ receptor sites, in analogy to baclofen, can be used as muscle relaxants in spinal spasticity, multiple sclerosis and cerebral palsy; in addition they are expected to be active in trigeminus neuralgia, in drug withdrawal syndroms, and as analgesics. Compounds combining $GABA_B$ and $GABA_A$ receptor agonist properties may be active as antidepressants.

Antagonists on the other hand are expected to act as muscle stimulants and to be active in muscular atrophy, dystrophy and weakness associated for example with Parkinsonism and Erb's paralysis. As $GABA_B$ receptor antagonists are expected to increase glutamate and aspartate release during neurotransmission, a positive effect in information processing in the brain may be anticipated.

As a representative compound of the invention the compound of example 8 has been shown to be active at the $GABA_B$ receptor site with an $IC_{50}$-value of 35 nM, as a muscle relaxant (rotarod mice $ID_{50}$-value of 6-9 mg/kg i.p.), as an analgesic (phenylquinone writhing in mice $ED_{50}$-value of 4 mg/kg p.o.) and as an anticonvulsant (audiogenic seizures in DBA/2 mice, $ID_{50}$-value of 6 mg/kg i.p.). At a dose of 200 mg/kg i.p. no deaths were observed.

Compounds of the invention depending on their pharmacological profiles are claimed to be active as muscle relaxants, muscle stimulants, analgesics, anticonvulsants, antidepressants, nootropics and drugs reducing drug withdrawal syndroms.

The aforementioned advantageous properties render the compounds of this invention of great value as specific therapeutic agents for mammals including man.

The present invention relates also to pharmaceutical preparations containing compounds of the formula I or pharmaceutically acceptable salts thereof. These preparations may be used especially in the above-mentioned indications, if they are administered orally or parenterally, such as intravenously, intramuscularly or subcutaneously. The necessary dose depends on the particular disorder to be treated, its severity and the duration of therapy. The number and quantity of the individual doses and also the administration scheme is best determined on the basis of an individual examination of the host concerned, these methods being known to those skilled in the art. As a rule, however, a therapeutically active quantity of a compound of this invention is in the dosage range of about 0.1 to 10 mg/kg body weight per day. The pharmaceutical preparations are manufactured according to known methods, using standard auxiliary substances.

The following examples are intended to illustrate the invention and are not to be construed as being limitations thereon. All parts wherever given are parts by weight. If not mentioned otherwise, all evaporations under reduced pressure are preferably performed between about 20 and 130 mbar. The data designated as $^{31}P$ are phosphorus-31-NMR data.

EXAMPLE 1

(a) A solution of 5.4 g of ethyl 3-aminopropyl (diethoxymethyl)-phosphinate in 30 ml of 36% aqueous hydrochloric acid is heated to reflux under an atmosphere of nitrogen for a period of 3 hours. The reaction mixture is then allowed to cool to room temperature, concentrated under reduced pressure and co-evaporated twice with 10 ml of water under reduced pressure. The crude product is dissolved in 50 ml of dry methanol, the solution is cooled to 0° C., and 5 ml of propylene oxide is added dropwise. The mixture is concentrated under reduced pressure, triturated with 50 ml of ethanol and the crude product is filtered off. Recrystallisation from a mixture of ethanol and methanol yields 3-aminopropylphosphonous acid, m.p. 209°-213° C., $^{31}P = +28.2$ ppm ($D_2O$).

(b) The starting material can be prepared as follows:

A solution of 20 g of ethyl (diethoxymethyl)phosphonite (Aust. J. Chem. 33, 292 (1980)) and 5 g of acrylonitrile in 25 ml of ethanol is added to a stirred mixture of 1 g of sodium hydride (50% dispersion in oil) in 25 ml of ethanol at 0° C. under an atmosphere of nitrogen. The reaction mixture is allowed to warm to room temperature and stirred for 4 hours. 1 ml of glacial acetic acid is added and the mixture is concentrated under reduced pressure. The resulting crude product is dissolved in 50 ml of ethyl acetate, washed twice with 26 ml of water, and the organic extract is dried over magnesium sulphate, and then concentrated under reduced pressure. The crude product is distilled under reduced pressure to give ethyl 2-cyanoethyl (diethoxymethyl)phosphinate, b.p. 114° C./0.01 mbar, $^{31}P = +40.8$ ppm (CDCl$_3$).

This product can also be prepared as follows:

A solution of 10.6 g of ethyl (diethoxymethyl)phosphonite in 9 g of hexamethyldisilazane is heated to reflux under an atmosphere of nitrogen for a period of 3 hours. The reaction mixture is allowed to cool to 20° C. and then distilled under reduced pressure to give ethyl trimethylsilyl (diethoxymethyl)phosphonite, b.p. 51° C. at 0.01 mbar, $^{31}P = +146.9$ ppm (CDCl$_3$).

Reaction of ethyl trimethylsilyl(diethoxymethyl)phosphonite with 3-chloropropionitrile yields ethyl 2-cyanoethyl(diethoxymethyl) phosphinate, identical with the above compound.

A solution of 9.6 g of ethyl 2-cyanoethyl(diethoxymethyl)phosphinate in 450 ml of ethanol is added to 82 g of an 8% solution of ammonia in ethanol. To this is added 5 ml of Raney Nickel and the resulting mixture is hydrogenated at 1 bar until the theoretical amount of hydrogen has been taken up. The mixture is then filtered, the filtrate is concentrated under reduced pressure and the crude product is distilled to give ethyl 3-aminopropyl(diethoxymethyl) phosphinate, b.p. 150° C./0.01 mbar, $^{31}P = +46.4$ ppm (CDCl$_3$).

EXAMPLE 2

Further compounds, which are prepared according to the process hereinbefore described and illustrated in Example 1, are, for example, those of the following table:

| | R$^1$ | R$^2$ | R$^3$ |
|---|---|---|---|
| (a) | hydrogen | 4-chlorophenyl | hydrogen (RS, R or S forms) |
| (b) | hydrogen | 2-methylphenyl | hydrogen |
| (c) | hydrogen | 4-bromophenyl | hydrogen |
| (d) | hydrogen | 2-methoxyphenyl | hydrogen |
| (e) | hydrogen | 3,4-dimethoxyphenyl | hydrogen |
| (f) | hydrogen | 4-trifluoromethyl-phenyl | hydrogen |
| (g) | hydrogen | 3,4-dichlorophenyl | hydrogen |
| (h) | hydrogen | sec-butyl | hydrogen |
| (i) | hydrogen | n-octyl | hydrogen |
| (j) | hydrogen | 4-chlorobenzyl | hydrogen |

EXAMPLE 3

(a) A solution of 14.1 g of ethyl 3-amino-1-methylpropyl(diethoxymethyl)phosphinate in 50 ml of 36% aqueous hydrochloric acid is heated to reflux for a period of 5 hours. The reaction mixture is then allowed to cool to room temperature, concentrated under reduced pressure and co-evaporated twice with 20 ml of water under reduced pressure. The crude product is then dissolved in 20 ml of water, washed twice with 20 ml of diethyl ether and the aqueous layer is then separated and evaporated under reduced pressure. The crude product is dissolved in 50 ml of dry ethanol and 5 ml of propylene oxide is added dropwise to produce an oily solid. This product is then passed down an ion exchange resin column made from Dowex 50W-X2 and eluted with water. Fractions showing a ninhydrin positive test are combined and evaporated under reduced pressure to give 3-amino-1-methyl-propylphosphonous acid as a hygroscopic solid m.p. 55°-60° C., $^{31}P = +35.1$ ppm (D$_2$O).

(b) The starting material may be prepared as follows:

A solution of 23.5 g of ethyl (diethoxymethyl)phosphonite and 6.7 g of crotononitrile in 30 ml of dry ethanol is added to a stirred mixture of 1.2 g of sodium hydride (50% dispersion in oil) in 30 ml of ethanol at 0° C. under an atmosphere of nitrogen. The reaction mixture is allowed to warm to room temperature and stirred for 4 hours. 1 ml of glacial acetic acid is added and the mixture concentrated under reduced pressure. The resulting crude product is dissolved in 50 ml of ethyl acetate, washed twice with 25 ml of water, and the organic extract is dried over magnesium sulphate, and then concentrated under reduced pressure. The crude product is distilled under reduced pressure to give ethyl 2-cyano-1-methyl-ethyl(diethoxymethyl)phosphinate, b.p. 116° C./0.01 mbar, $^{31}P = +42.2$ and $+42.0$ ppm (CDCl$_3$).

A solution of 17.0 g of ethyl 1-methyl-2-cyanoethyl(diethoxymethyl)phosphinate in 150 ml of ethanol is added to 155.0 g of an 8% solution of ammonia in ethanol. To this are added 10 ml of Raney Nickel and the resulting mixture is hydrogenated at 1 bar until the theoretical amount of hydrogen has been taken up. The mixture is then filtered and the filtrate is concentrated under reduced pressure and the crude product is distilled under reduced pressure to give ethyl 3-amino-1-methylpropyl(diethoxymethyl)phosphinate, b.p. 140° C./0.01 mbar, $^{31}P = +47.0$ and $+46.7$ ppm (CDCl$_3$).

EXAMPLE 4

(a) A solution of 6.0 g of ethyl 3-amino-2-methylpropyl(diethoxymethyl)phosphinate in 30 ml of 36% aqueous hydrochloric acid is heated to reflux for a period of 7 hours. The reaction mixture is then allowed to cool to room temperature, concentrated under reduced pressure and co-evaporated twice with 10 ml of water under reduced pressure. The crude product is dissolved in 50 ml of dry ethanol and 5 ml of propylene oxide is added dropwise. The precipitated solid is collected by filtration and dried to give 3-amino-2-methylpropylphosphonous acid monohydrate, m.p. 96°-100° C., $^{31}P = +25.8$ ppm (D$_2$O).

(b) The starting material may be prepared as follows:

A solution of 23.5 g of ethyl (diethoxymethyl)phosphonite and 6.7 g of methacrylonitrile in 30 ml of ethanol is added dropwise to a stirred mixture of 1.2 g of sodium hydride (50% dispersion in oil) in 30 ml of ethanol at 0° C. under an atmosphere of nitrogen. The reaction mixture is allowed to warm to room temperature and stirred for 4 hours. 1 ml of glacial acetic acid is added and the mixture is concentrated under reduced pressure. The resulting crude product is dissolved in 50 ml of ethyl acetate, washed twice with 25 ml of water, and the organic extract is dried over magnesium sulphate, and then concentrated under reduced pressure. The crude product is distilled under reduced pressure to give ethyl-2-cyanopropyl(diethoxymethyl)phosphinate, b.p. 116° C./0.01 mbar, $^{31}P = +40.4$ and $+40.3$ ppm (CDCl$_3$).

A solution of 17.0 g of ethyl 2-cyanopropyl(diethoxymethyl)phosphinate in 150 ml of ethanol is added to 155 g of an 8% solution of ammonia in ethanol. To this are added 10 ml of Raney Nickel and the resulting mixture is hydrogenated at 1 bar until the theoretical amount of hydrogen has been taken up. The mixture is then filtered, the filtrate is concentrated under reduced pressure and the crude product is distilled under reduced pressure to give ethyl 3-amino-2-methylpropyl(diethoxymethyl)phosphinate, b.p. 150° C./0.01 mbar, $^{31}P = +45.8$ and $+45.7$ ppm (CDCl$_3$).

EXAMPLE 5

(a) A solution of 9.8 g of ethyl 3-aminobutyl(diethoxymethyl)phosphinate in 100 ml of 36% aqueous hydrochloric acid is heated to reflux for a period of 1 hour. The reaction mixture is then allowed to cool to room temperature, concentrated under reduced pressure and co-evaporated twice with 10 ml of water under reduced pressure. The crude product is then dissolved in 20 ml of water, washed twice with 20 ml of diethyl ether and the aqueous layer is then separated and evaporated under reduced pressure. The crude product is passed down a column of Dowex 50W-X2 eluted with water. Fractions showing a ninhydrin positive test are combined and evaporated under reduced pressure to give 3-aminobutylphosphonous acid ($\frac{1}{3}$M H$_2$O), m.p. 195°–200° C., $^{31}$P = +28.1 ppm (D$_2$O).

(b) The starting material may be prepared as follows:

15.0 g of ethyl trimethylsilyl(diethoxymethyl)phosphonite are added dropwise to a stirred solution of 3.9 g of methyl vinyl ketone under an atmosphere of nitrogen at room temperature. The mixture is then heated to 50° C. for a period of 1 hour. The mixture is then allowed to cool to room temperature, 25 ml of chloroform is then added followed by 10 ml water and this mixture is vigorously stirred for a period of 0.5 h. The organic layer is then separated, dried over magnesium sulphate and concentrated under reduced pressure and the crude product distilled under reduced pressure to give ethyl 3-oxobutyl(diethoxymethyl)phosphinate, b.p. 130°–135° C./0.02 mbar, $^{31}$P = +45.3 ppm (CDCl$_3$).

To a solution of 8.0 g of ethyl 3-oxobutyl(diethoxymethyl)phosphinate in 100 ml of methanol is added 22.8 g of ammonium acetate and 1.3 g of sodium cyanoborohydride. The mixture is stirred under an atmosphere of nitrogen at room temperature for a period of 2.5 h, and then left to stand overnight. The mixture is then acidified to pH 2 with the requisite amount of dilute hydrochloric acid and the methanol is evaporated under reduced pressure. The crude product is dissolved in 25 ml of water, washed twice with 20 ml of diethyl ether and the aqueous phase is then made alkaline to pH 12 with potassium hydroxide. The solution is then saturated with sodium chloride and extracted with 3×25 ml of dichloromethane. The organic phase is dried over magnesium sulphate, filtered and evaporated under reduced pressure and the crude product distilled to give ethyl 3-aminobutyl(diethoxymethyl)phosphinate, b.p. 150° C./0.01 mbar, $^{31}$P = +46.1 ppm (CDCl$_3$).

EXAMPLE 6

(a) A solution of 17.9 g of ethyl 3-amino-1-(4-chlorophenyl)propyl(diethoxymethyl)phosphinate in 200 ml of 36% aqueous hydrochloric acid is heated to reflux for a period of 6 hours. The reaction mixture is then allowed to cool to room temperature, concentrated under reduced pressure and co-evaporated twice with 50 ml of water under reduced pressure. The crude product is then dissolved in 50 ml of water, washed twice with 20 ml of diethyl ether and the aqueous layer is then separated and evaporated under reduced pressure. The crude product is then dissolved in 50 ml of ethanol and 5 ml of propylene oxide is added dropwise. The precipitated solid is collected by filtration and dried to give 3-amino-1-(4-chlorophenyl)propylphosphonous acid, m.p. 210°–220° C., $^{31}$P = +29.6 ppm (D$_2$O).

(b) The starting material may be prepared as follows:

A solution of 25.8 g of ethyl (diethoxymethyl)phosphonite and 18.0 g of 4-chlorocinnamonitrile in 100 ml of ethanol is added to a stirred mixture of 1.2 g of sodium hydride (50% dispersion in oil) in 30 ml of ethanol at 0° C. under an atmosphere of nitrogen. The reaction mixture is allowed to warm to room temperature and stirred for 4 hours. 1 ml of glacial acetic acid is added and the mixture is concentrated under reduced pressure. The resulting crude product is dissolved in 50 ml of ethyl acetate, washed twice with 25 ml of water and the organic extract is dried over magnesium sulphate, and then concentrated under reduced pressure. The crude product is distilled under reduced pressure to give ethyl 1-(4-chlorophenyl)-2-cyanoethyl(diethoxymethyl)phosphinate, b.p. 180°–200° C./0.02 mbar, $^{31}$P = +37.9 and +37.8 ppm (CDCl$_3$).

A solution of 20 g of ethyl 1-(4-chlorophenyl)-2-cyanoethyl(diethoxymethyl)phosphinate in 85 ml of ethanol is added to 131 g of an 8% solution of ammonia in ethanol. To this are added 8.5 ml of Raney Nickel and the resulting mixture is hydrogenated at 1 bar until the theoretical amount of hydrogen has been taken up. The mixture is then filtered, the filtrate is concentrated under reduced pressure and the crude product is distilled under reduced pressure to give ethyl 3-amino-1-(4-chlorophenyl)propyl(diethoxymethyl)phosphinate, b.p. 190° C./0.02 mbar, $^{31}$P = +41.5 and +41.3 ppm (CDCl$_3$).

EXAMPLE 7

(a) A solution of 10.5 g of ethyl 3-amino-3-(4-chlorophenyl)propyl(diethoxymethyl)phosphinate in 100 ml of 36% aqueous hydrochloric acid is heated to reflux for a period of 2 hours. The reaction mixture is then allowed to cool to room temperature, concentrated under reduced pressure, and co-evaporated twice with 25 ml of water under reduced pressure. The crude product is then dissolved in 20 ml of water, washed twice with 20 ml of diethyl ether and the aqueous layer is then separated and evaporated under reduced pressure. The crude product is dissolved in 50 ml of ethanol and 5 ml of propylene oxide is added dropwise. The precipitated solid is collected by filtration and dried to give 3-amino-3-(4-chlorophenyl)propylphosphonous acid, m.p. 284°–286° C., $^{31}$P = +27.2 ppm (D$_2$O).

(b) The starting material may be prepared as follows:

17.7 g of ethyl trimethylsilyl(diethoxymethyl)phosphonite is added dropwise to a stirred solution of 11.7 g of 4-chlorophenyl vinyl ketone under an atmosphere of nitrogen, at room temperature. The reaction mixture is stirred for a period of 1 hour, 25 ml of chloroform is added followed by 10 ml of water and this mixture is vigorously stirred for a period of 0.5 h. The organic layer is then separated, dried over magnesium sulphate and concentrated under reduced pressure to give ethyl 2-4-chlorobenzoyl-ethyl(diethoxymethyl)phosphinate as an oil, $^{31}$P = +45.5 ppm (CDCl$_3$).

To a solution of 25.4 g of ethyl 2-(4-chlorobenzoyl)ethyl(diethoxymethyl)phosphinate in 200 ml of methanol is added 52 g of ammonium acetate and 4.23 g of sodium cyanoborohydride. The mixture is stirred under an atmosphere of nitrogen at room temperature for a period of 3 days. The mixture is then acidified to pH 2 with the requisite amount of dilute hydrochloric acid and the methanol is evaporated under reduced pressure. The crude product is dissolved in 25 ml of water, washed twice with 20 ml of diethyl ether and the aqueous layer is then made alkaline to pH 12 with potassium hydroxide. The solution is then saturated with sodium chloride and extractd with 3×25 ml of dichloromethane. The organic phase is dried over magnesium sulphate and then evaporated under reduced pressure to give ethyl 3-amino-3-(4-chlorophenyl)propyl(diethoxymethyl)phosphinate as a viscous oil, $^{31}P=45.9$ ppm (CDCl$_3$).

EXAMPLE 8

(a) A solution of 5.0 g of ethyl 3-amino-2-(4-chlorophenyl)propyl(diethoxymethyl)phosphinate in 60 ml of 36% aqueous hydrochloric acid is heated to reflux for a period of 1 h. The reaction mixture is then allowed to cool to room temperature, concentrated under reduced pressure and co-evaporated twice with 20 ml of water under reduced pressure. The crude product is dissolved in 20 ml of water, washed twice with 20 ml of diethyl ether and the aqueous layer is then separated and evaporated under reduced pressure. The crude product is dissolved in 50 ml ethanol and 5 ml of propylene oxide is added dropwise. The precipitated solid is collected by filtration and dried to give 3-amino-2-(4-chlorophenyl)propylphosphonous acid (½M H$_2$O), m.p. 235°-240° C., $^{31}P=+23.9$ ppm (D$_2$O).

(b) The starting material may be prepared as follows:
To a solution of 1.16 g of diisopropylamine in 40 ml of tetrahydrofuran at −78° C. under an atmosphere of nitrogen are added 7.2 ml of a 1.6M solution of n-butyllithium in hexane. This solution is then stirred for a period of 10 minutes at this temperature, after which time a solution of 2.0 g of ethyl (diethoxymethyl)methylphosphinate in 20 ml of tetrahydrofuran is added. This mixture is then stirred for a period of 1 hour at −78° C. after which time a solution of 1.75 g of 4-chloro-β-nitrostyrene in 20 ml of tetrahydrofuran is introduced. This mixture is then allowed to warm to room temperature when 40 ml of a saturated ammonium chloride solution is added. The aqueous layer is then extracted with 2×25 ml of diethyl ether and the organic extracts are combined and dried over magnesium sulphate. The solvent is then evaporated under reduced pressure and the crude product chromatographed on silica gel using ethyl acetate as an eluent to give ethyl 2-(4-chlorophenyl)-3-nitropropyl(diethoxymethyl)phosphinate as a viscous oil, $^{31}P=+42.2$ and +41.8 ppm (CDCl$_3$).

A solution of 8.0 g of ethyl 2-(4-chlorophenyl)-3-nitropropyl(diethoxymethyl)phosphinate in 70 ml of ethanol is added to 64 g of an 8% solution of ammonia in ethanol. To this are added 8 ml of Raney Nickel and the resulting mixture is hydrogenated at 1 bar until the theoretical amount of hydrogen has been taken up. The mixture is then filtered and the filtrate is concentrated under reduced pressure to give ethyl 3-amino-2-(4-chlorophenyl)propyl(diethoxymethyl) phosphinate as a viscous oil, $^{31}P=+44.2$ and 44.1 ppm (CDCl$_3$).

EXAMPLE 9

(a) A solution of 1.4 g of ethyl 3-amino-2-cyclohexylpropyl(diethoxymethyl)phosphinate in 30 ml of 36% aqueous hydrochloric acid is heated to reflux for a period of 1 hour. The reaction mixture is then allowed to cool to room temperature, concentrated under reduced pressure and co-evaporated twice with 10 ml of water under reduced pressure. The crude product is then dissolved in 20 ml of water washed twice with 20 ml of diethyl ether and the aqueous layer is then separated and evaporated under reduced pressure. The crude product is dissolved in 50 ml of dry ethanol and 5 ml of propylene oxide is added dropwise. The precipitated solid is collected by filtration and dried to give 3-amino-2-cyclohexylpropylphosphonous acid m.p. 235°-240° C., $^{31}P=28.2$ ppm (D$_2$O).

(b) The starting material may be prepared as follows:
To a solution of 5.8 g of diisopropylamine in 40 ml of tetrahydrofuran at −78° C. under an atmosphere of nitrogen are added 35.7 ml of a 1.6M solution of n-butyllithium in hexane. This solution is then stirred for a period of 10 minutes at this temperature, after which time a solution of 10.0 g of ethyl (diethoxymethyl)methylphosphinate in 20 ml of tetrahydrofuran is added. This mixture is then stirred for a period of 1 hour at −78° C. after which time a solution of 8.5 g of β-nitrostyrene in 20 ml of tetrahydrofuran is introduced. This mixture is then allowed to warm to room temperature when 40 ml of a saturated ammonium chloride solution is added. The aqueous layer is then extracted with 2×25 ml of diethyl ether and the organic extracts are combined and dried over magnesium sulphate. The solvent is then evaporated under reduced pressure and the crude product chromatographed on silica gel using ethyl acetate as an eluent to give ethyl 3-nitro-2-phenylpropyl(diethoxymethyl)phosphinate as a viscous oil, $^{31}P=+42.3$ and +42.0 ppm (CDCl$_3$).

A solution of 1.0 g of ethyl 3-nitro-2-phenylpropyl(diethoxymethyl)phosphinate in 25 ml of ethanol is added to 25 g of an 8% solution of ammonia in ethanol. To this are added 0.5 ml of Raney Nickel and the resulting mixture hydrogenated at 1 bar until the theoretical amount of hydrogen has been taken up. The mixture is then filtered and the filtrate is concentrated under reduced pressure to give ethyl 3-amino-2-phenylpropyl(diethoxymethyl)phosphinate as a viscous oil, $^{31}P=+44.4$ ppm (CDCl$_3$).

A solution of 3.45 g of ethyl 3-amino-2-phenylpropyl(diethoxymethyl)phosphinate in 25 ml of tertiary butanol is added to 2.0 g of 5% rhodium in alumina, suspended in 25 ml of tertiary butanol. The resulting mixture is hydrogenated at an atmosphere of 150 bar and temperature of 100° C. for a period of 20 hours. The mixture is then filtered and the filtrate is concentrated under reduced pressure. The crude product is chromatographed on silica gel using ethanol as eluent to give ethyl 3-amino-2-cyclohexylpropyl(diethoxymethyl)phosphinate as a viscous oil, $^{31}P=47.1$ and +47.0 ppm (CDCl$_3$).

EXAMPLE 10

(a) A solution of 3.5 g of ethyl 3-amino-2-benzylpropyl(diethoxymethyl)phosphinate in 35 ml of 36% aqueous hydrochloric acid is heated to reflux for a period of 3 hours. The reaction mixture is then allowed to cool to room temperature, concentrated under reduced pressure and co-evaporated twice with 20 ml of water under reduced pressure. The crude product is dissolved in 20 ml of water, washed twice with 20 ml of diethyl ether and the aqueous layer is then separated and evaporated under reduced pressure. The crude product is dissolved in 50 ml ethanol and 5 ml of propylene oxide is added dropwise. The precipitated solid is collected by filtration and dried to give 3-amino-2-benzylpropylphosphonous acid, m.p. 205°-212° C., $^{31}P=+26.1$ ppm (D$_2$O).

(b) The starting material may be prepared as follows:
To a solution of 0.97 g of diisopropylamine in 40 ml of tetrahydrofuran at −78° C. under an atmosphere of nitrogen are added 6.0 ml of a 1.6M solution of n-butyllithium in hexane. This solution is then stirred for a period of 10 minutes at this temperature, after which time a solution of 2.0 g of ethyl 2-cyanoethyl(diethoxymethyl)phosphinate in 10 ml of tetrahydrofuran is added. This mixture is then stirred for a period of 1 hour at −78° C. after which time a solution of 1.4 g of benzyl bromide in 10 ml of tetrahydrofuran is introduced. This mixture is then allowed to warm to room temperature when 40 ml of a saturated ammonium chloride solution is added. The aqueous layer is then extracted with 2×25 ml of diethyl ether and the organic extracts are combined and dried over magnesium sulphate. The solvent is then evaporated under reduced pressure and the crude product chromatographed on silica gel using ethyl acetate as an eluent to give ethyl 2-benzyl-2-cyanoethyl(diethoxymethyl)phosphinate as a viscous oil, $^{31}P = +40.7$ and $+40.5$ ppm (CDCl$_3$).

A solution of 3.5 g of ethyl 2-benzyl-2-cyanoethyl(diethoxymethyl)phosphinate in 50 ml of ethanol is added to 25 g of an 8% solution of ammonia in ethanol. To this are added 2 ml of Raney Nickel and the resulting mixture is hydrogenated at 1 bar until the theoretical amount of hydrogen has been taken up. The mixture is then filtered and the filtrate is concentrated under reduced pressure to give ethyl 3-amino-2-benzylpropyl(diethoxymethyl)phosphinate as a viscous oil, $^{31}P = +46.3$ ppm (CDCl$_3$).

EXAMPLE 11

A solution of 5.0 g of ethyl 3-amino-2-(4-chlorophenyl)propyl(diethoxymethyl)phosphinate in 60 ml of 36% aqueous hydrochloric acid is heated to reflux for a period of 1 hour. The reaction mixture is then allowed to cool to room temperature, concentrated under reduced pressure, and co-evaporated three times with 20 ml of water under reduced pressure to give 3-amino-2-(4-chlorophenyl)propylphosphonous acid hydrochloride, as a hygroscopic solid, $^{31}P = +30.1$ ppm (D$_2$O).

EXAMPLE 12

A solution of 0.25 g of 3-amino-2-(4-chlorophenyl)propylphosphonous acid in 10 ml of 0.1M sodium hydroxide solution is stirred at room temperature for a period of 1 hour, and then concentrated under reduced pressure to give sodium 3-amino-2-(4-chlorophenyl)propylphosphinate as a hygroscopic solid, $^{31}P = +26.0$ ppm (D$_2$O).

EXAMPLE 13

(a) A solution of 4.0 g of ethyl 3-amino-2-phenylpropyl(diethoxymethyl)phosphinate in 40 ml of 36% aqueous hydrochloric acid is heated to reflux for a period of 2 h. The reaction mixture is then allowed to cool to room temperature, concentrated under reduced pressure and co-evaporated twice with 20 ml of water under reduced pressure. The crude product is dissolved in 20 ml of water, washed twice with 20 ml of diethyl ether and the aqueous layer is then separated and evaporated under reduced pressure. The crude product is dissolved in 50 ml ethanol and 5 ml of propylene oxide is added dropwise. The precipitated solid is collected by filtration and dried to give 3-amino-2-phenylpropylphosphonous acid m.p. 228°–235° C., $^{31}P = +24.3$ ppm (D$_2$O).

(b) The starting material may be prepared as follows:

To a solution of 5.8 g of diisopropylamine in 40 ml of tetrahydrofuran at −78° C. under an atmosphere of nitrogen are added 35.7 ml of a 1.6M solution of n-butyllithium in hexane. This solution is then stirred for a period of 10 minutes at this temperature, after which time a solution of 10.0 g of ethyl (diethoxymethyl)methylphosphinate in 20 ml of tetrahydrofuran is added. This mixture is then stirred for a period of 1 hour at −78° C. after which time a solution of 8.5 g of β-nitrostyrene in 20 ml of tetrahydrofuran is introduced. This mixture is then allowed to warm to room temperature when 40 ml of a saturated ammonium chloride solution is added. The aqueous layer is then extracted with 2×25 ml of diethyl ether and the organic extracts are combined and dried over magnesium sulphate. The solvent is then evaporated under reduced pressure and the crude product chromatographed on silica gel using ethyl acetate as an eluent to give ethyl 3-nitro-2-phenylpropyl(diethoxymethyl)phosphinate as a viscous oil, $^{31}P = +42.4$ and $+42.0$ ppm (CDCl$_3$).

A solution of 5.7 g of ethyl 3-nitro-2-phenylpropyl(diethoxymethyl)phosphinate in 60 ml of ethanol is added to 50 g of an 8% solution of ammonia in ethanol. To this are added 9 ml of Raney Nickel and the resulting mixture is hydrogenated at 1 bar until the theoretical amount of hydrogen has been taken up. The mixture is then filtered and the filtrate is concentrated under reduced pressure to give ethyl 3-amino-2-phenylpropyl(diethoxymethyl)phosphinate as a viscous oil, $^{31}P = +44.4$ ppm (CDCl$_3$).

EXAMPLE 14

(a) A solution of 4.4 g of ethyl 3-amino-2-(4-fluorophenyl)propyl(diethoxymethyl)phosphinate in 40 ml of 36% aqueous hydrochloric acid is heated to reflux for a period of 2 h. The reaction mixture is then allowed to cool to room temperature, concentrated under reduced pressure and co-evaporated twice with 20 ml of water under reduced pressure. The crude product is dissolved in 20 ml of water, washed twice with 20 ml of diethyl ether and the aqueous layer is then separated and evaporated under reduced pressure. The crude product is dissolved in 50 ml ethanol and 5 ml of propylene oxide is added dropwise. The precipitated solid is collected by filtration and dried to give 3-amino-2-(4-fluorophenyl)propylphosphonous acid (¼M H$_2$O), m.p. 225°–235° C., $^{31}P = +24.1$ ppm (D$_2$O).

(b) The starting material may be prepared as follows:

To a solution of 5.8 g of diisopropylamine in 40 ml of tetrahydrofuran at −78° C. under an atmosphere of nitrogen are added 35.7 ml of a 1.6M solution of n-butyllithium in hexane. This solution is then stirred for a period of 10 minutes at this temperature, after which time a solution of 10.0 g of ethyl(diethoxymethyl)methylphosphinate in 20 ml of tetrahydrofuran is added. This mixture is then stirred for a period of 1 hour at −78° C. after which time a solution of 7.96 g of 4-fluoro-β-nitrostyrene in 20 ml of tetrahydrofuran is introduced. This mixture is then allowed to warm to room temperature when 40 ml of a saturated ammonium chloride solution is added. The aqueous layer is then extracted with 2×25 ml of diethyl ether and the organic extracts are combined and dried over magnesium sulphate. The solvent is then evaporated under reduced pressure and the crude product chromatographed on silica gel using ethyl acetate as an eluent to give ethyl 2-(4-fluorophenyl)-3-nitropropyl(diethoxymethyl)phosphinate as a viscous oil, $^{31}P = +42.3$ and $+41.9$ ppm (CDCl$_3$).

A solution of 5.0 g of ethyl 2-(4-fluorophenyl)-3-nitropropyl(diethoxymethyl)phosphinate in 50 ml of ethanol is added to 40 g of an 8% solution of ammonia in ethanol. To this are added 7 ml of Raney Nickel and the resulting mixture is hydrogenated at 1 bar until the theoretical amount of hydrogen has been taken up. The mixture is then filtered and the filtrate is concentrated under reduced pressure to give ethyl 3-amino-2-(4-fluorophenyl)propyl(diethoxymethyl)phosphinate as a viscous oil, $^{31}P = +44.4$ ppm (CDCl$_3$).

EXAMPLE 15

(a) A solution of 3.7 g of ethyl 3-amino-2-(4-methylphenyl)propyl(diethoxymethyl)phosphinate in 40 ml of 36% aqueous hydrochloric acid is heated to reflux for a period of 1 h. The reaction mixture is then allowed to cool to room temperature, concentrated under reduced pressure and co-evaporated twice with 20 ml of water under reduced pressure. The crude product is dissolved in 20 ml of water, washed twice with 20 ml of diethyl ether and the aqueous layer is then separated and evaporated under reduced pressure. The crude product is dissolved in 50 ml ethanol and 5 ml of propylene oxide is added dropwise. The precipitated solid is collected by filtration and dried to give 3-amino-2-(4-methylphenyl)propylphosphonous acid, m.p. 250°-255° C., $^{31}P = +24.5$ ppm (D$_2$O).

(b) The starting material may be prepared as follows:

To a solution of 8.7 g of diisopropylamine in 40 ml of tetrahydrofuran at −78° C. under an atmosphere of nitrogen are added 53.6 ml of a 1.6M solution of n-butyllithium in hexane. This solution is then stirred for a period of 10 minutes at this temperature, after which time a solution of 15.0 g of ethyl(diethoxymethyl)methylphosphinate in 20 ml of tetrahydrofuran is added. This mixture is then stirred for a period of 1 hour at −78° C. after which time a solution of 11.6 g of 4-methyl-β-nitrostyrene in 20 ml of tetrahydrofuran is introduced. This mixture is then allowed to warm to room temperature when 40 ml of a saturated ammonium chloride solution is added. The aqueous layer is then extracted with 2×25 ml of diethyl ether and the organic extracts are combined and dried over magnesium sulphate. The solvent is then evaporated under reduced pressure and the crude product chromatographed on silica gel using ethyl acetate as an eluent to give ethyl 2-(4-methylphenyl)-3-nitropropyl(diethoxymethyl)phosphinate as a viscous oil, $^{31}P = +42.5$ and $+42.1$ ppm (CDCl$_3$).

A solution of 6.5 g of ethyl 2-(4-methylphenyl)-3-nitropropyl(diethoxymethyl)phosphinate in 60 ml of ethanol is added to 52 g of an 8% solution of ammonia in ethanol. To this are added 8 ml of Raney Nickel and the resulting mixture is hydrogenated at 1 bar until the theoretical amount of hydrogen has been taken up. The mixture is then filtered and the filtrate is concentrated under reduced pressure to give ethyl 3-amino-2-(4-methylphenyl)propyl(diethoxymethyl)phosphinate as a viscous oil, $^{31}P = +44.6$ ppm (CDCl$_3$).

EXAMPLE 16

(a) A solution of 4.6 g of ethyl 3-amino-2-(4-methoxyphenyl)propyl(diethoxymethyl)phosphinate in 30 ml of 36% aqueous hydrochloric acid is heated to reflux for a period of 1 hour. The reaction mixture is then allowed to cool to room temperature, concentrated under reduced pressure and co-evaporated twice with 20 ml of water under reduced pressure. The crude product is dissolved in 20 ml of water, washed twice with 20 ml of diethyl ether and the aqueous layer is then separated and evaporated under reduced pressure. The crude product is dissolved in 50 ml ethanol and 5 ml of propylene oxide is added dropwise. The precipitated solid is collected by filtration and dried to give 3-amino-2-(4-methoxyphenyl)propylphosphonous acid (½M H$_2$O), m.p. 260°-265° C., $^{31}P = +24.5$ ppm (D$_2$O).

(b) The starting material may be prepared as follows:

To a solution of 8.7 g of diisopropylamine in 40 ml of tetrahydrofuran at −78° C. under an atmosphere of nitrogen are added 53.6 ml of a 1.6M solution of n-butyllithium in hexane. This solution is then stirred for a period of 10 minutes at this temperature, after which time a solution of 15.0 g of ethyl (diethoxymethyl)methylphosphinate in 20 ml of tetrahydrofuran is added. This mixture is then stirred for a period of 1 hour at −78° C. after which time a solution of 12.8 g of 4-methoxy-β-nitrostyrene in 20 ml of tetrahydrofuran is introduced. This mixture is then allowed to warm to room temperature when 40 ml of a saturated ammonium chloride solution is added. The aqueous layer is then extracted with 2×25 ml of diethyl ether and the organic extracts are combined and dried over magnesium sulphate. The solvent is then evaporated under reduced pressure and the crude product chromatographed on silica gel using ethyl acetate as an eluent to give ethyl 2-(4-methoxyphenyl)-3-nitropropyl(diethoxymethyl)phosphinate as a viscous oil, $^{31}P = +42.4$ and $+42.1$ ppm (CDCl$_3$).

A solution of 6.6 g of ethyl 2-(4-methoxyphenyl)-3-nitropropyl(diethoxymethyl)phosphinate in 50 ml of ethanol is added to 52 g of an 8% solution of ammonia in ethanol. To this are added 8 ml of Raney Nickel and the resulting mixture is hydrogenated at 1 bar until the theoretical amount of hydrogen has been taken up. The mixture is then filtered and the filtrate is concentrated under reduced pressure to give ethyl 3-amino-2-(4-methoxyphenyl)propyl(diethoxymethyl)phosphinate as a viscous oil, $^{31}P = +44.5$ ppm (CDCl$_3$).

EXAMPLE 17

Preparation of 10,000 tablets each containing 10 mg of the active ingredient with a formula as follows:

| | |
|---|---|
| 3-aminopropylphosphonous acid | 100.00 g |
| Lactose | 1,157.00 g |
| Corn starch | 75.00 g |
| Polyethylene glycol 6,000 | 75.00 g |
| Magnesium stearate | 18.00 g |
| Purified water | q.s. |

Procedure: All the powders are passed through a screen with openings of 0.6 mm. Then the drug substance, lactose, magnesium stearate and half of the starch are mixed in a suitable mixer. The other half of the starch is suspended in 40 ml of water and the suspension added to the boiling solution of the polyethylene glycol in 150 ml of water. The paste formed is added to the powders which are granulated, if necessary, with an additional amount of water. The granulate is dried overnight at 35° C., broken on a screen with 1,2 mm openings and compressed into tablets with 6.4 mm diameter, uppers bisected.

EXAMPLE 18

Preparation of 10,000 capsules each containing 25 mg of the active ingredient with a formula as follows:

| | |
|---|---|
| 3-amino-2-(4-chlorophenyl)- | 250.0 g |

| -continued | |
|---|---|
| propylphosphonous acid | |
| Lactose | 1,750.0 g |

Procedure: All the powders are passed through a screen with openings of 0.6 mm. Then the drug substance is placed in a suitable mixer and mixed with the lactose until homogenous. No. 3 capsules are filled with 200 mg using a capsule filling machine.

Similarly prepared are tablets and capsules comprising as active ingredients 10–100 mg of other compounds of the invention, e.g. those given in the examples herein.

We claim:

1. Ethyl 2-(4-chlorophenyl)-3-nitropropyl(diethoxymethyl)phosphinate.
2. Ethyl 2-phenyl-3-nitropropyl(diethoxymethyl)phosphinate.
3. Ethyl 2-(4-fluorophenyl)-3-nitropropyl(diethoxymethyl)phosphinate.
4. Ethyl 2-(4-methylphenyl)-3-nitropropyl(diethoxymethyl)phosphinate.
5. Ethyl 2-(4-methoxyphenyl)-3-nitropropyl(diethoxymethyl)phosphinate.

* * * * *